United States Patent
Shiki et al.

(10) Patent No.: US 9,173,632 B2
(45) Date of Patent: Nov. 3, 2015

(54) ULTRASONIC DIAGNOSIS SYSTEM AND IMAGE DATA DISPLAY CONTROL PROGRAM

(75) Inventors: Eiichi Shiki, Otawara (JP); Yoshitaka Mine, Nasushiobara (JP)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 13/336,118

(22) Filed: Dec. 23, 2011

(65) Prior Publication Data

US 2012/0113111 A1    May 10, 2012

Related U.S. Application Data

(63) Continuation of application No. PCT/JP2010/060978, filed on Jun. 28, 2010.

(30) Foreign Application Priority Data

Jun. 30, 2009  (JP) .................................. 2009-155323

(51) Int. Cl.
*G06T 15/00*     (2011.01)
*A61B 8/08*      (2006.01)
(Continued)

(52) U.S. Cl.
CPC . *A61B 8/08* (2013.01); *A61B 8/463* (2013.01); *A61B 8/466* (2013.01); *A61B 8/483* (2013.01);
(Continued)

(58) Field of Classification Search
CPC ........ A61B 8/08; A61B 8/483; G06T 19/003; G06T 2207/30101
See application file for complete search history.

(56) References Cited

U.S. PATENT DOCUMENTS 5,793,310 A * 8/1998 Watanabe et al. ........ 340/995.14
6,252,599 B1 * 6/2001 Natsuko et al. ............... 345/419
(Continued)

FOREIGN PATENT DOCUMENTS

JP      2001-14495      1/2001
JP      2004-283373     10/2004
(Continued)

OTHER PUBLICATIONS

Nakano F., Machine translated Japanese patent application, "Image Diagnostic Device, Image Display Device and Three-Dimensional Image Display Method", publication No. 2005-11093, date of publication: Apr. 28, 2005.*

(Continued)

*Primary Examiner* — James A Thompson
*Assistant Examiner* — Tapas Mazumder
(74) *Attorney, Agent, or Firm* — Oblon, McClelland, Maier & Neustadt, L.L.P.

(57) ABSTRACT

An ultrasonic diagnosis system that generates virtual endoscopic image data on a lumen of an organ of an object based on volume data acquired by three-dimensional scanning of the object, includes: a unit that sets a three-dimensional region of interest for the volume data; a unit that sets a center line of the lumen of the organ in the volume data based on the acquired volume data; a unit that detects a reference point at which a reference plane of the three-dimensional region of interest and the center line intersect with each other; a unit that sets a viewpoint and a view direction based on the reference point; a virtual endoscopic image data generating unit that processes the volume data based on the viewpoint and the view direction to generate the virtual endoscopic image data; and a display unit that displays the generated virtual endoscopic image data.

16 Claims, 12 Drawing Sheets

(51) Int. Cl.
*G06T 7/00* (2006.01)
*G06T 19/00* (2011.01)
*A61B 8/00* (2006.01)

(52) U.S. Cl.
CPC .............. *G06T 7/0083* (2013.01); *G06T 19/00* (2013.01); *G06T 19/003* (2013.01); *G06T 2207/10132* (2013.01); *G06T 2207/30101* (2013.01)

(56) References Cited

U.S. PATENT DOCUMENTS

| | | | | |
|---|---|---|---|---|
| 2001/0010514 | A1* | 8/2001 | Ishino | 345/158 |
| 2002/0042566 | A1* | 4/2002 | Matsuzaki et al. | 600/407 |
| 2004/0249270 | A1* | 12/2004 | Kondo et al. | 600/425 |
| 2005/0004467 | A1* | 1/2005 | Shiina et al. | 600/449 |
| 2005/0008209 | A1* | 1/2005 | Matsumoto | 382/128 |
| 2008/0044054 | A1* | 2/2008 | Kim et al. | 382/100 |
| 2008/0055308 | A1* | 3/2008 | Dekel et al. | 345/421 |
| 2009/0187104 | A1* | 7/2009 | Yamagata | 600/443 |
| 2009/0240150 | A1* | 9/2009 | Wang et al. | 600/443 |
| 2010/0012859 | A1* | 1/2010 | Claereboudt | 250/492.3 |
| 2010/0045664 | A1* | 2/2010 | Ishida | 345/419 |

FOREIGN PATENT DOCUMENTS

| | | | |
|---|---|---|---|
| JP | 2005-110973 | | 4/2005 |
| JP | 2007-195685 | | 8/2007 |
| JP | 2009-056125 | * | 3/2009 |
| JP | 2009-165718 | | 7/2009 |
| WO | WO 2009/116465 A1 | | 9/2009 |

OTHER PUBLICATIONS

International Search Report mailed Jul. 20, 2010 in PCT/JP2010/060978 filed Jun. 28, 2010 (with English Translation).

English Translation of the International Preliminary Report on Patentability and Written Opinion issued Feb. 14, 2012 in PCT/JP2010/060978.

* cited by examiner

ULTRASONIC DIAGNOSIS SYSTEM AND IMAGE DATA DISPLAY CONTROL PROGRAM

CROSS-REFERENCE TO RELATED APPLICATIONS

This application is based upon and claims the benefit of priority from Japanese Patent Application No. 2009-155323 filed on Jun. 30, 2009 and PCT Application No. PCT/JP2010/060978 filed on Jun. 28, 2010, the entire contents of each of which are incorporated herein by reference.

FIELD

Embodiments described herein relate generally to an ultrasonic diagnosis system and image data display control program.

BACKGROUND

An ultrasonic diagnosis system acquires biological information by emitting an ultrasonic pulse and receiving a reflected ultrasonic wave from the object tissue. The ultrasonic pulse is generated in an oscillating element in an ultrasonic probe. The reflected ultrasonic wave depends on the acoustic impedance in the object tissue. The ultrasonic diagnosis system requires only a simple operation of bringing the ultrasonic probe into contact with the body surface of the object for displaying image data in real time. Thus, the system is widely used for morphologic and functional diagnosis of various organs.

In recent years, mechanically movable ultrasonic probes which has a one-dimensional array of oscillating elements, or ultrasonic probes which has a two-dimensional array of oscillating elements have enabled three-dimensional scanning of a diagnosis target part of the object. Three-dimensional image data or multi-planar reconstruction (MPR) image data can be generated from the three-dimensional data (volume data) acquired by the three-dimensional scanning and used for advanced diagnosis and treatment.

There have been proposed techniques of observing an inner surface of a lumen of an organ of an object by acquiring volume data concerning the lumen of the organ of the object by three-dimensional scan, setting a virtual viewpoint and a virtual view direction in the lumen of the organ, and producing virtual endoscopic (fly-through) image data representing the inner surface of the lumen of the organ viewed from the viewpoint (see Japanese Patent Laid-Open No. 2005-110973, for example).

According to these techniques, since endoscopic image data is generated based on the volume data externally acquired, invasion of the object during examination is significantly reduced. In addition, since the viewpoint and the view direction can be arbitrarily set in any lumens of organs including small alimentary canals and blood vessels to which an endoscope is difficult to insert, safe and efficient examination can be conducted with precision that cannot be achieved by conventional endoscopy.

By applying the process described in the above document to volume data acquired by an ultrasonic diagnosis system, virtual endoscopic image data can be observed in real time. Meanwhile, according to a common conventional method of setting a viewpoint and a view direction required to generate virtual endoscopic image data for volume data on a lumen of an organ, MPR image data comprising cross sectional images of the lumen of the organ formed by arbitrarily slicing the volume data is acquired, and the viewpoint and the view direction are set based on the MPR image data. However, in order to continuously observe the virtual endoscopic image data by moving the ultrasonic prove on the body surface of the object, the complicated process described above has to be repeated to update the viewpoint and the view direction as the ultrasonic probe moves. Thus, it is difficult to observe the virtual endoscopic image data in real time.

The present invention has been devised in view of the problem described above. An object of the present invention is to provide an ultrasonic diagnosis system that generates virtual endoscopic image data based on volume data acquired from an object and ensures constant observation of the virtual endoscopic image data in a preferred direction even when an ultrasonic probe moves, and an image data display control program.

DETAILED DESCRIPTION

Embodiments of an ultrasonic diagnosis system are explained below with reference to the accompanying drawings.

According to one embodiment, an ultrasonic diagnosis system that generates virtual endoscopic image data on a lumen of an organ of an object based on volume data acquired by three-dimensional scanning of the object, includes: a region-of-interest setting unit that sets a three-dimensional region of interest for the volume data; a center line setting unit that sets a center line of the lumen of the organ in the volume data based on the acquired volume data; a reference point detecting unit that detects a reference point at which a reference plane of the three-dimensional region of interest and the center line intersect with each other; a viewpoint/view-direction setting unit that sets a viewpoint and a view direction based on the reference point; a virtual endoscopic image data generating unit that processes the volume data based on the viewpoint and the view direction to generate the virtual endoscopic image data; and a display unit that displays the generated virtual endoscopic image data.

In the embodiment described below, a two-dimensional array ultrasonic probe, in which a plurality of oscillating elements are two-dimensionally arranged, is used to acquire three-dimensional B-mode data, and volume data is generated based on the three-dimensional B-mode data. However, the present invention is not limited to such volume data. For example, volume data acquired by mechanically moving an ultrasonic probe having a one-dimensional array of oscillating elements may be used. Alternatively, volume data may be generated based on ultrasonic data other than the B-mode data, such as color Doppler data.

The three-dimensional scanning described below includes real-time three-dimensional scanning, that is, a so-called 4D scanning. If the 4D scanning is performed by moving an ultrasonic probe over a body surface of a patient, a three-dimensional image that spatially and temporally changes in real time can be generated.

(System Configuration)

Figure 1:
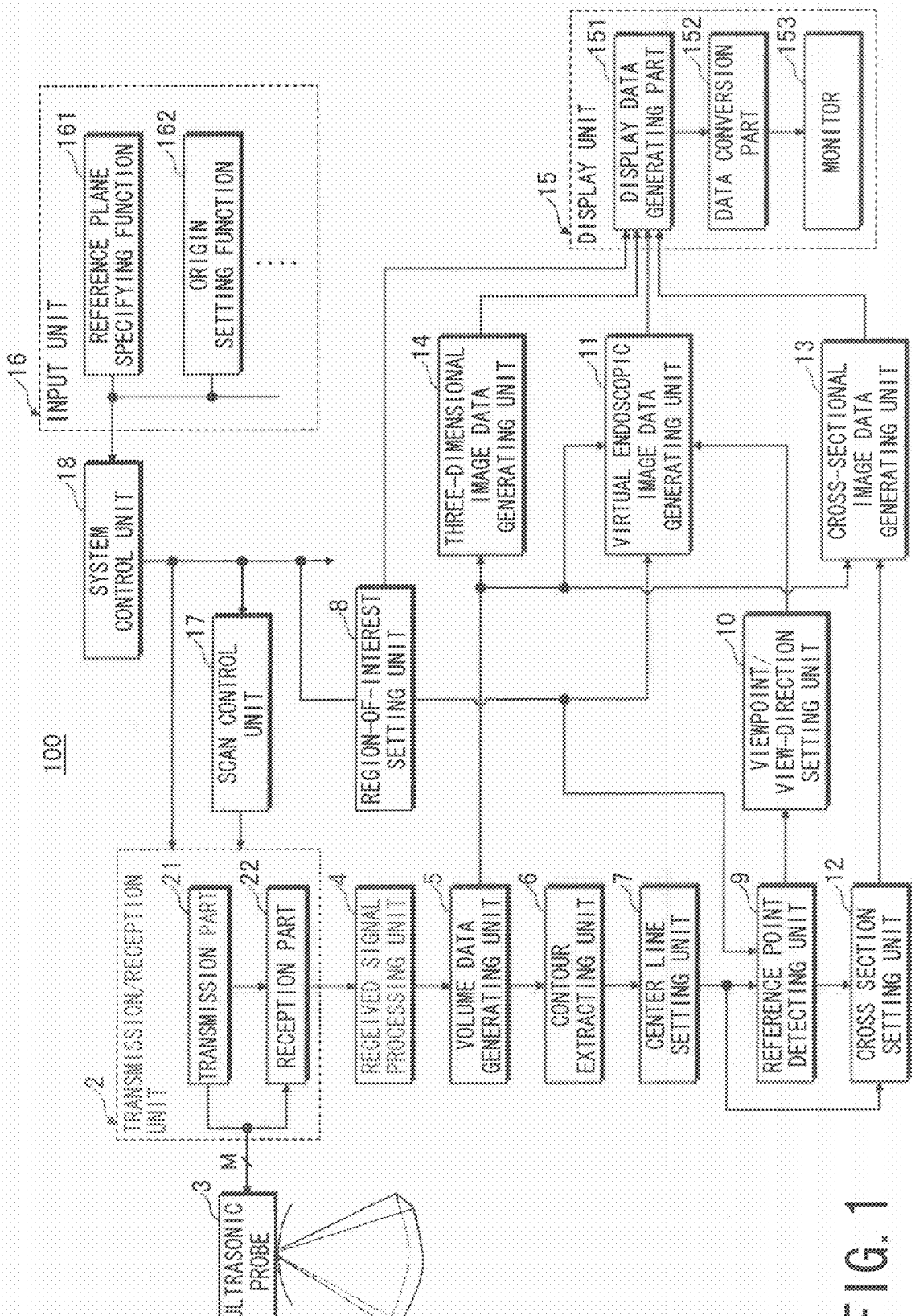
FIG. 1 is a block diagram showing a configuration of the whole of an ultrasonic diagnosis system according to an embodiment of the present invention.
Figure 2:
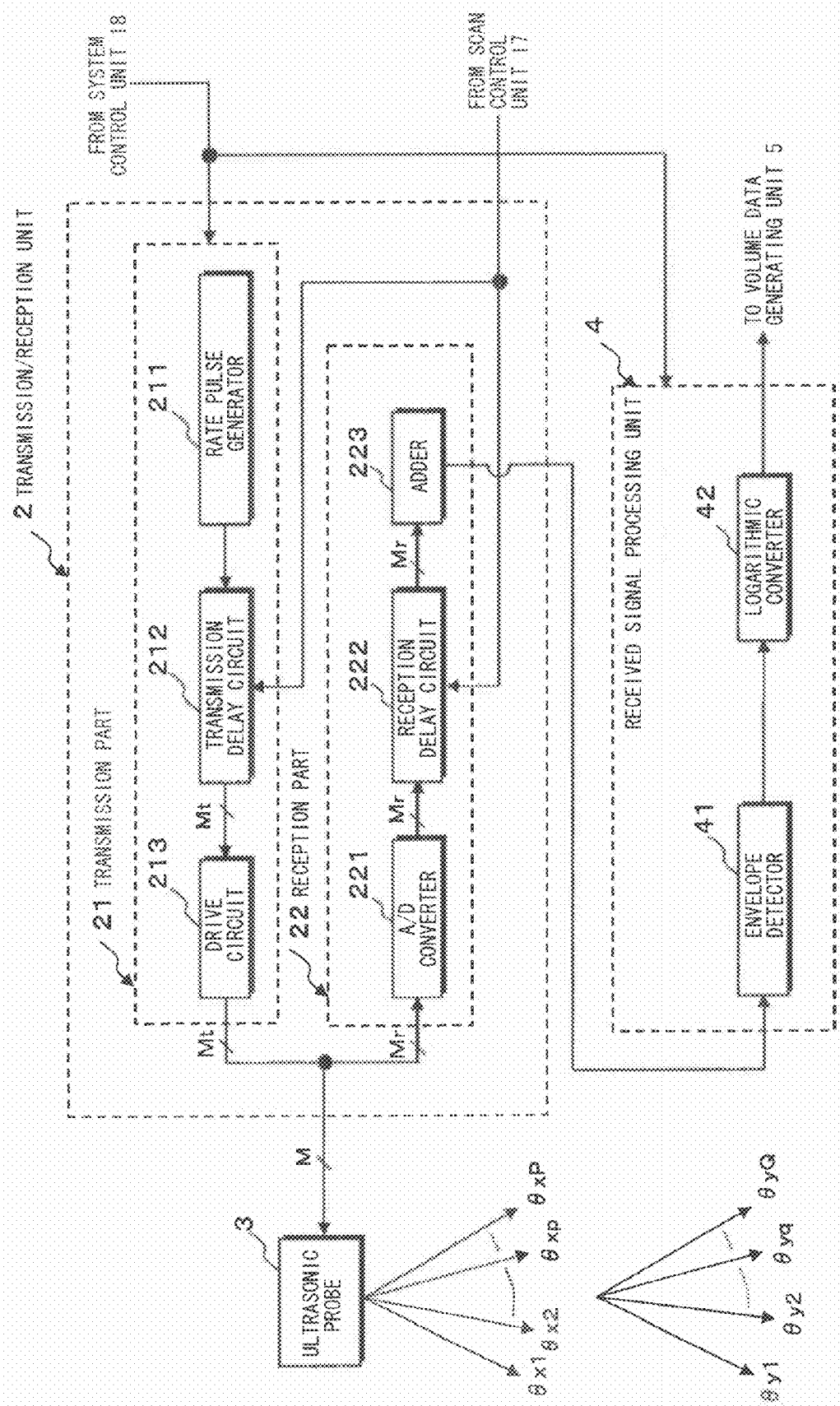
FIG. 2 is a block diagram showing a specific configuration of a transmission/reception unit and a received signal processing unit of the ultrasonic diagnosis system according to the embodiment, FIGS. 3A to 3C include diagrams for illustrating a direction of arrangement of oscillating elements of an ultrasonic probe and an ultrasonic wave transmission/reception direction according to the embodiment.

A configuration of the ultrasonic diagnosis system according to this embodiment will be described with reference to FIGS. 1 to 9. FIG. 1 is a block diagram showing a configuration of the whole of the ultrasonic diagnosis system 100, FIG. 2 is a block diagram showing a specific configuration of a transmission/reception unit 2 and a received signal processing unit 4 of the ultrasonic diagnosis system, and FIG. 4 is a block diagram showing a specific configuration of a volume data generating unit 5 of the ultrasonic diagnosis system.

An ultrasonic diagnosis system 100 according to this embodiment shown in FIG. 1 includes an ultrasonic probe 3, a transmission/reception unit 2, a received signal processing unit 4, and a volume data generating unit 5.

The ultrasonic probe 3 includes a plurality of oscillating elements that transmits an ultrasonic pulse (transmission ultrasonic wave) to a three-dimensional region including a lumen of an organ of an object and converts an ultrasonic reflection wave (reception ultrasonic wave) received from the object into an electrical signal (received signal).

The transmission/reception unit 2 supplies a drive signal to the oscillating elements to transmit the ultrasonic pulse in a predetermined direction in the object, and performs phase-adjusting and summation of the plurality of channels of received signals from the oscillating elements.

The received signal processing unit 4 processes the phase-adjusted and summed received signals to generate B-mode data as ultrasonic data.

The volume data generating unit 5 arranges the B-mode data obtained by the three-dimensional scanning of the object in a direction corresponding to the ultrasonic wave transmission/reception direction to generate three-dimensional data (volume data).

The ultrasonic diagnosis system 100 further includes a contour extracting unit 6, a region-of-interest setting unit 8, a reference point detecting unit 9, a viewpoint/view-direction setting unit 10 and a virtual endoscopic image data generating unit 11.

The contour extracting unit 6 extracts a contour of the lumen of the organ represented by the volume data based on a voxel value of the volume data.

The center line setting unit 7 sets a central axis (referred to as a center line hereinafter) of the lumen of the organ based on the contour information on the lumen of the organ.

The region-of-interest setting unit 8 sets a three-dimensional region of interest of a predetermined size for the volume data.

The reference point detecting unit 9 detects an intersection (referred to as a reference point hereinafter) of a reference plane of the three-dimensional region of interest and the center line.

The viewpoint/view-direction setting unit 10 sets a viewpoint and a view direction required to generate virtual endoscopic image data based on the reference point.

The virtual endoscopic image data generating unit 11 performs rendering of the volume data based on the viewpoint and the view direction described above to generate the virtual endoscopic image data.

The ultrasonic diagnosis system 100 still further includes a cross section setting unit 12, a cross-sectional image data generating unit 13, a three-dimensional image data generating unit 14, a display unit 15, an input unit 16 and a scan control unit 17.

The cross section setting unit 12 sets an axial cross section, for the volume data, that includes the reference point and that is perpendicular to the center line.

The cross-sectional image data generating unit 13 extracts a voxel from the volume data in the axial cross section to generate cross-sectional image data that represents an axial cross section of the lumen of the organ.

The three-dimensional image data generating unit 14 performs rendering of the volume data to generate three-dimensional image data.

The display unit 15 displays the virtual endoscopic image data, the cross-sectional image data, the three-dimensional image data or the like.

The input unit 16 is used to input object information or various command signals and to set a volume data generation condition.

The scan control unit 17 controls an ultrasonic wave transmission/reception direction during the three-dimensional scanning, and the system control unit 18 collectively controls the units described above.

In the following, configurations and functions of the units of the ultrasonic diagnosis system 100 according to this embodiment described above will be described in more detail.

The ultrasonic probe 3 has a two-dimensional array of M oscillating elements (not shown) at a tip end part thereof, which is brought into contact with a body surface of an object to transmit and receive an ultrasonic wave. The oscillating element is an electro-acoustic converting element, which converts an electrical pulse (drive signal) into an ultrasonic pulse (transmission ultrasonic wave) during transmission, and converts an ultrasonic reflection wave (reception ultrasonic wave) into an electrical received signal during reception. Each of the oscillating elements is connected to the transmission/reception unit 2 by a multi-core cable having M channels (not shown). Although this embodiment described below concerns a case where an ultrasonic probe 3 is used for sector scan, an ultrasonic probe adapted for linear scan or convex scan may also be used.

The transmission/reception unit 2, as shown in FIG. 2, includes a transmission part 21 that supplies a drive signal to the oscillating elements of the ultrasonic probe 3 and a reception part 22 that performs phase-adjusting and summation of the received signals from the oscillating elements.

The transmission part 21 has a rate pulse generator 211, a transmission delay circuit 212 and a drive circuit 213. The rate pulse generator 211 generates a rate pulse that determines a pulse repetition interval of the transmission ultrasonic wave and supplies the rate pulse to the transmission delay circuit 212. The transmission delay circuit 212 is formed by the same number of independent delay circuits as the number of Mt oscillating elements used for transmission. The transmission delay circuit 212 provides the rate pulse with a focusing delay time required to focus the transmission ultrasonic wave at a predetermined depth and a deflecting delay time required to transmit the ultrasonic wave in a predetermined direction ($\theta xp$, $\theta yq$), and supplies the resulting rate pulse to the drive circuit 213. Of the M oscillating elements two-dimensionally arranged in the ultrasonic probe 3, the Mt oscillating elements selected for transmission are driven by a drive signal generated based on the rate pulse to emit the transmission ultrasonic wave into the object.

The reception part 22 has an A/D converter 221, a reception delay circuit 222 and an adder 223, which have Mr channels corresponding to Mr oscillating elements selected for reception among from the M oscillating elements in the ultrasonic probe 3. The A/D converter 221 converts Mr channels of received signals provided from the receiving oscillating elements into digital signals and passes the digital signals to the reception delay circuit 222.

The reception delay circuit 222 provides the Mr channels of received signals output from the A/D converter 221 with a converging delay time required to converge the reception ultrasonic wave from the predetermined depth and a deflecting delay time required to set a reception directivity in the direction ($\theta xp$, $\theta yq$), and the adder 223 sums the received signals from the reception delay circuit 222. That is, the reception delay circuit 222 and the adder 223 cooperate to perform phase-adjusting and summation of the received signals from the direction ($\theta xp$, $\theta yq$). By controlling the delay times, the reception delay circuit 222 and the adder 223 in the reception part 22 can simultaneously provide reception directivities in a plurality of directions, that is, enable parallel simultaneous reception. The parallel simultaneous reception significantly reduces the time required for the three-dimensional scan. The transmission part 21 and the reception part 22 of the transmission/reception unit 2 described above may be partially provided in the ultrasonic probe 3.

Figure 3A:
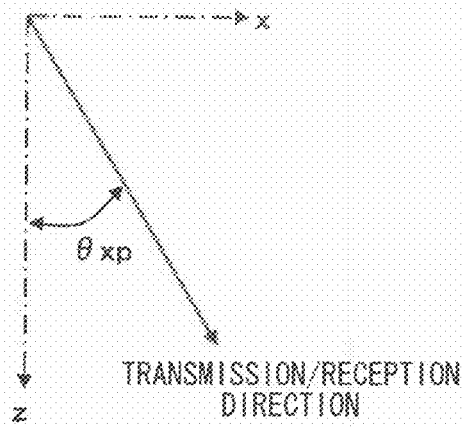
Figure 3B:
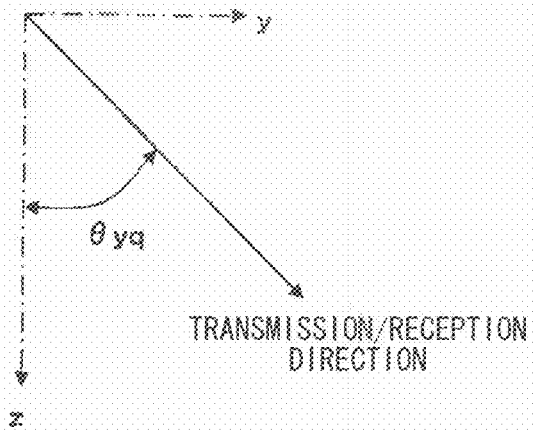
Figure 3C:
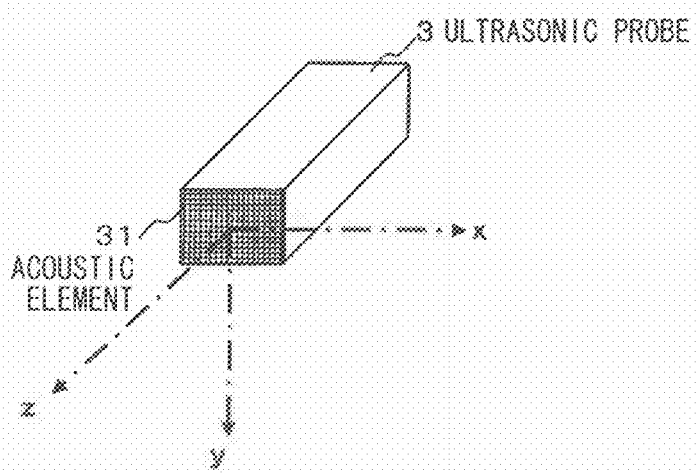
Figure 4:
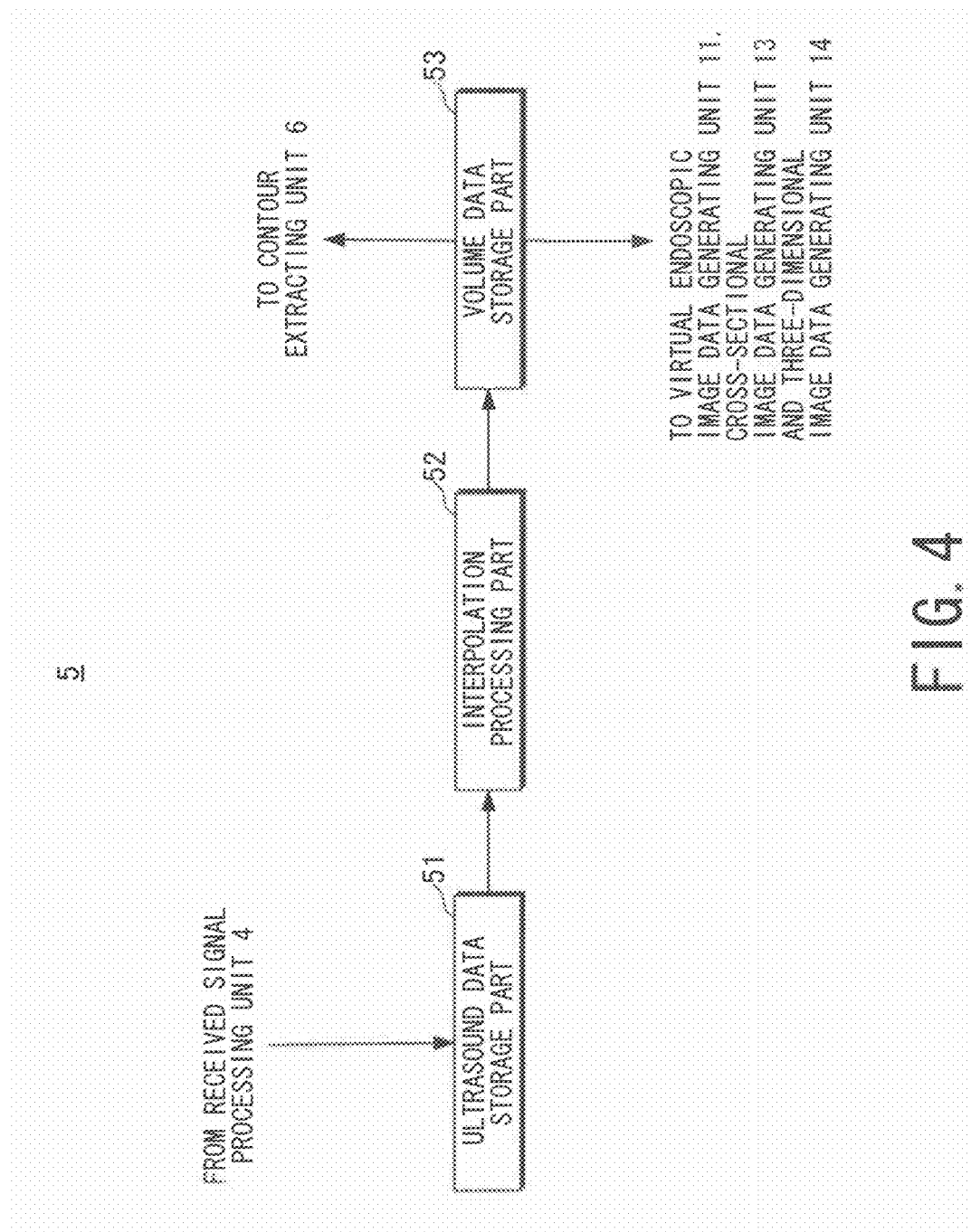
FIG. 4 is a block diagram showing a specific configuration of a volume data generating unit of the ultrasonic diagnosis system according to the embodiment, FIGS. 5A to 5C include diagrams showing volume data generated by a volume data generating unit according to the embodiment and a three-dimensional region of interest set for the volume data by a region-of-interest setting unit according to the embodiment, FIGS. 6A and 6B include diagrams showing a specific example of a reference point detected in a reference plane of the three-dimensional region of interest by a reference point detecting unit according to the embodiment and a viewpoint and a view direction set based on the reference point by a viewpoint/view-direction setting unit.

FIGS. 3A to 3C show the ultrasonic wave transmission/reception direction ($\theta xp$, $\theta yq$) in an orthogonal coordinate system [x, y, z] whose z axis corresponds to a central axis of the ultrasonic probe 3. As can be seen from FIG. 3C, oscillating elements 31 are two-dimensionally arranged in an x-axis direction and a y-axis direction. The coordinate $\theta xp$ indicates an angle of the ultrasonic wave transmission/reception direction projected on an x-z plane with respect to the z axis, and the coordinate $\theta yq$ indicates an angle of the ultrasonic wave transmission/reception direction projected on a y-z plane with respect to the z axis. The delay times of the transmission delay circuit 212 in the transmission part 21 and the reception delay circuit 222 in the reception part 22 are controlled by a scan control signal supplied from the scan control unit 17, and ultrasonic wave transmission/reception occurs successively in directions ($\theta xp$, $\theta yq$)=($\theta xp=\theta x1+(p-1)\Delta\theta x$ (p=1 to P), $\theta yq=\theta y1+(q-1)\Delta\theta y$ (q=1 to Q)) of the three-dimensional region including the diagnosis target part (lumen of the organ) of the object.

Referring back to FIG. 2, the received signal processing unit 4 has a function of processing the phase-adjusted and summed received signals output from the adder 223 in the reception part 22 to generate B-mode data as ultrasonic wave data. The received signal processing unit 4 includes an envelope detector 41 that detects an envelope of the received signals, and a logarithmic converter 42 that performs logarithmic conversion of the received signals having been subjected to the envelope detection. The order of the envelope detector 41 and the logarithmic converter 42 can be reversed.

Next, a specific configuration of the volume data generating unit 5 shown in FIG. 1 will be described with reference to FIG. 4. The volume data generating unit 5 includes an ultrasonic wave data storage part 51, an interpolation processing part 52, and a volume data storage part 53.

The ultrasonic wave data storage part 51 sequentially stores a plurality of ultrasonic wave data sets (B-mode data) generated by the received signal processing unit 4 from the receptions signals obtained by three-dimensional scanning of the object along with auxiliary information on the ultrasonic wave transmission/reception direction ($\theta xp$, $\theta yq$) supplied from the system control unit 18. The interpolation processing part 52 arranges the plurality of ultrasonic wave data sets read from the ultrasonic wave data storage part 51 in relation to the ultrasonic wave transmission/reception direction ($\theta xp$, $\theta yq$) to generate three-dimensional ultrasonic wave data, and then interpolates between unequally spaced voxels of the three-dimensional ultrasonic wave data to generate volume data comprising isotropic voxels. The volume data storage part 53 stores the volume data.

Based on a spatial variation of voxel values of the volume data, the contour extracting unit 6 shown in FIG. 1 extracts a contour of an inner wall or outer wall of the lumen of the organ represented by the volume data. For example, the contour of the lumen of the organ can be extracted by spatially differentiating and integrating the volume data and performing subtraction between the differentiated volume data and the integrated volume data, or performing subtraction between the volume data yet to be differentiated and the differentiated volume data. Of course, various other processes can be used to extract the contour.

The center line setting unit 7 has a function of setting a center line of the lumen of the organ based on the data on the contour of the lumen of the organ extracted by the contour extracting unit 6. For example, the center line setting unit 7 generates a plurality of unit vectors in all three-dimensional angular directions with respect to an origin in the lumen of the organ represented by the volume data, the origin being set based on three-dimensional image data described later displayed on the display unit 15. Then, from among these unit vectors, the center line setting unit 7 selects a unit vector that is the most distant from the contour of the lumen of the organ, as a search vector.

Then, the center line setting unit 7 calculates a position of a center of gravity of a axial cross section of the lumen of the organ that is perpendicular to the search vector, and sets a new search vector at the position of the center of gravity by correcting the direction of the search vector so that the intersection of the search vector and the axial cross section of the lumen of the organ agrees with the position of the center of gravity. Then, the above-described procedure is repeated using the corrected search vector. Then, the resulting plurality of positions of the center of gravity determined along a longitudinal direction of the lumen of the organ are interconnected to form a center line of the lumen of the organ. Of course, various other processes can be used to set the center line of the lumen of the organ, and the process described in Japanese Patent Laid-Open No. 2004-283373 can also be used, for example.

Figure 5A:
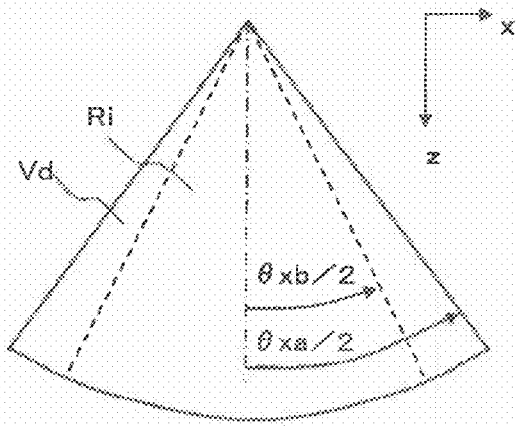
Figure 5B:
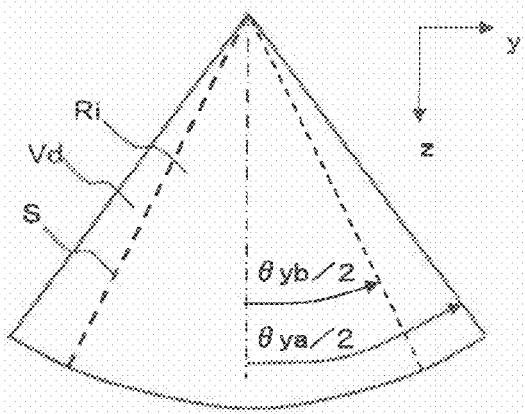
Figure 5C:
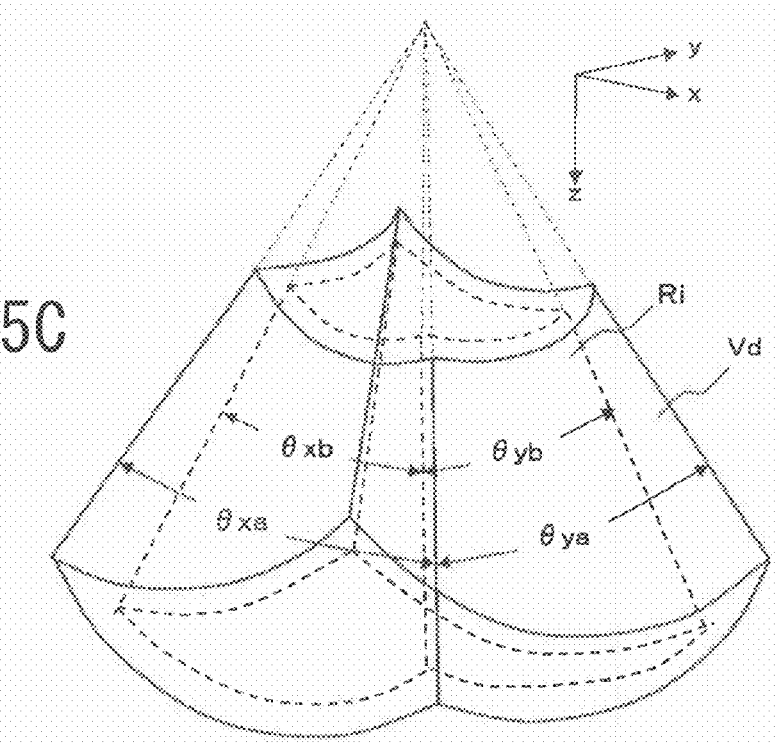

The region-of-interest setting unit 8 has a function of automatically setting a three-dimensional region of interest for the volume data acquired by three-dimensional scanning of the object. FIGS. 5A to 5C show volume data Vd acquired from the object, and a three-dimensional region of interest Ri set for the volume data. As described above, the volume data Vd is acquired in an x-directional scan range $\theta xa$ ($\theta xa=(P-1)\Delta\theta x$) and in a y-directional scan range $\theta ya$ ($\theta ya=(Q-1)\Delta\theta y$).

For the volume data Vd, the region-of-interest setting unit 8 sets the three-dimensional region of interest Ri in the x-directional range $\theta xb$ and the y-directional range $\theta yb$ ($\theta xb \leq \theta xa$, $\theta yb \leq \theta ya$) based on a volume data generation condition supplied from the input unit 16 via the system control unit 18. The ranges $\theta xb$ and $\theta yb$ described above may be set based on the size of the volume data so that $\theta xb/\theta xa$ and $\theta yb/\theta ya$ assume predetermined values, or may be set to be predetermined values regardless of the size of the volume data.

Referring back to FIG. 1, the reference point detecting unit 9 detects a reference point at which a reference plane of the three-dimensional region of interest specified via the input unit 16 and the center line of the lumen of the organ set by the center line setting unit 7 intersect with each other.

The reference plane may be set by specifying, via the input unit 16, a side face of the three-dimensional region of interest that intersects with the lumen of the organ represented by the volume data. Alternatively, by automatically detecting a side face of the three-dimensional region of interest that intersects with the lumen of the organ, the detected side face may be set as the reference plane.

The viewpoint/view-direction setting unit 10 sets a viewpoint and a view direction required to generate virtual endoscopic image data based on the reference point on the reference plane detected by the reference point detecting unit 9 and a tangent line of the center line at the reference point. More specifically, the viewpoint/view-direction setting unit 10 detects the tangential direction of the center line set by the center line setting unit 7 at the reference point and determines a point at a predetermined distance from the reference point in the direction of the tangent line as the viewpoint and a direction from the viewpoint to the reference point as the view direction.

Figure 6A:
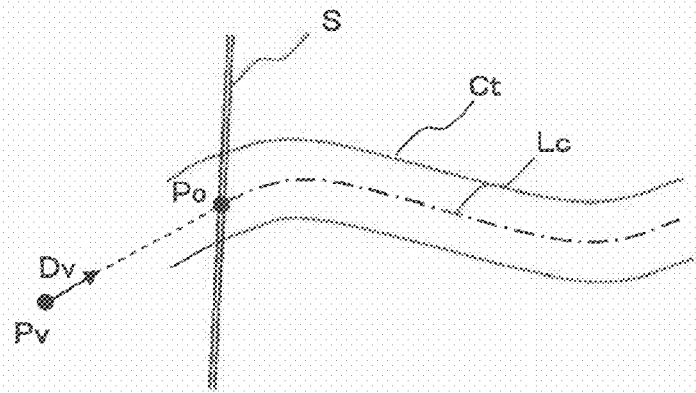
Figure 6B:
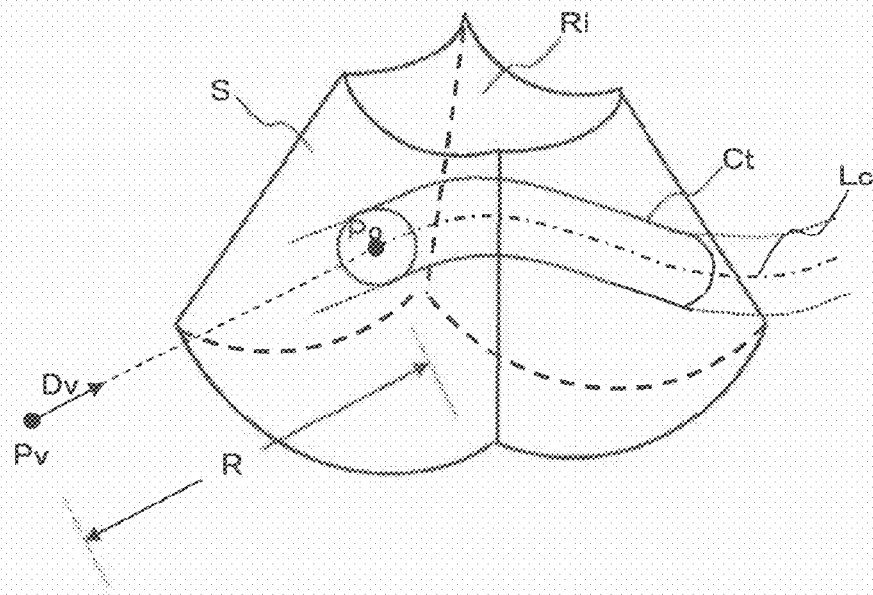

Next, the reference point detected by the reference point detecting unit 9 and the viewpoint and the view direction set by the viewpoint/view-direction setting unit 10 will be described in more detail with reference to FIGS. 6A and 6B. As described above with reference to FIGS. 5A to 5C, the region-of-interest setting unit 8 sets a three-dimensional region of interest Ri of a predetermined size (ranges $\theta xb$ and $\theta yb$) for the volume data Vd acquired by three-dimensional scanning of an object, and the center line setting unit 7 sets a center line Lc based on information on a contour Ct of a lumen of the organ of the object represented by volume data Vd. Then, the reference point detecting unit 9 detects a reference point Po at which a reference plane S of the three-dimensional region of interest Ri and the center line Lc intersect with each other. Then, the viewpoint/view-direction setting unit 10 detects the direction of a tangent line of the center line Lc at the reference point Po, and determines a point away from the reference point Po in the direction of the tangent line by a distance R as a viewpoint Pv and also determines a direction from the viewpoint Pv to the reference point Po as a view direction Dv.

Referring back to FIG. 1 again, the virtual endoscopic image data generating unit 11 includes a calculation circuit and a storage circuit (both not shown). The storage circuit previously stores a calculation program for producing the virtual endoscopic image data from the volume data. The calculation circuit reads the volume data on the object from the volume data storage part 53 in the volume data generating unit 5 and the calculation program from the storage circuit, and then generates the virtual endoscopic image data by performing rendering of the volume data based on information on the three-dimensional region of interest supplied from the region-of-interest setting unit 8 and information on the viewpoint and the view direction supplied from the viewpoint/view-direction setting unit 10.

Figure 7:
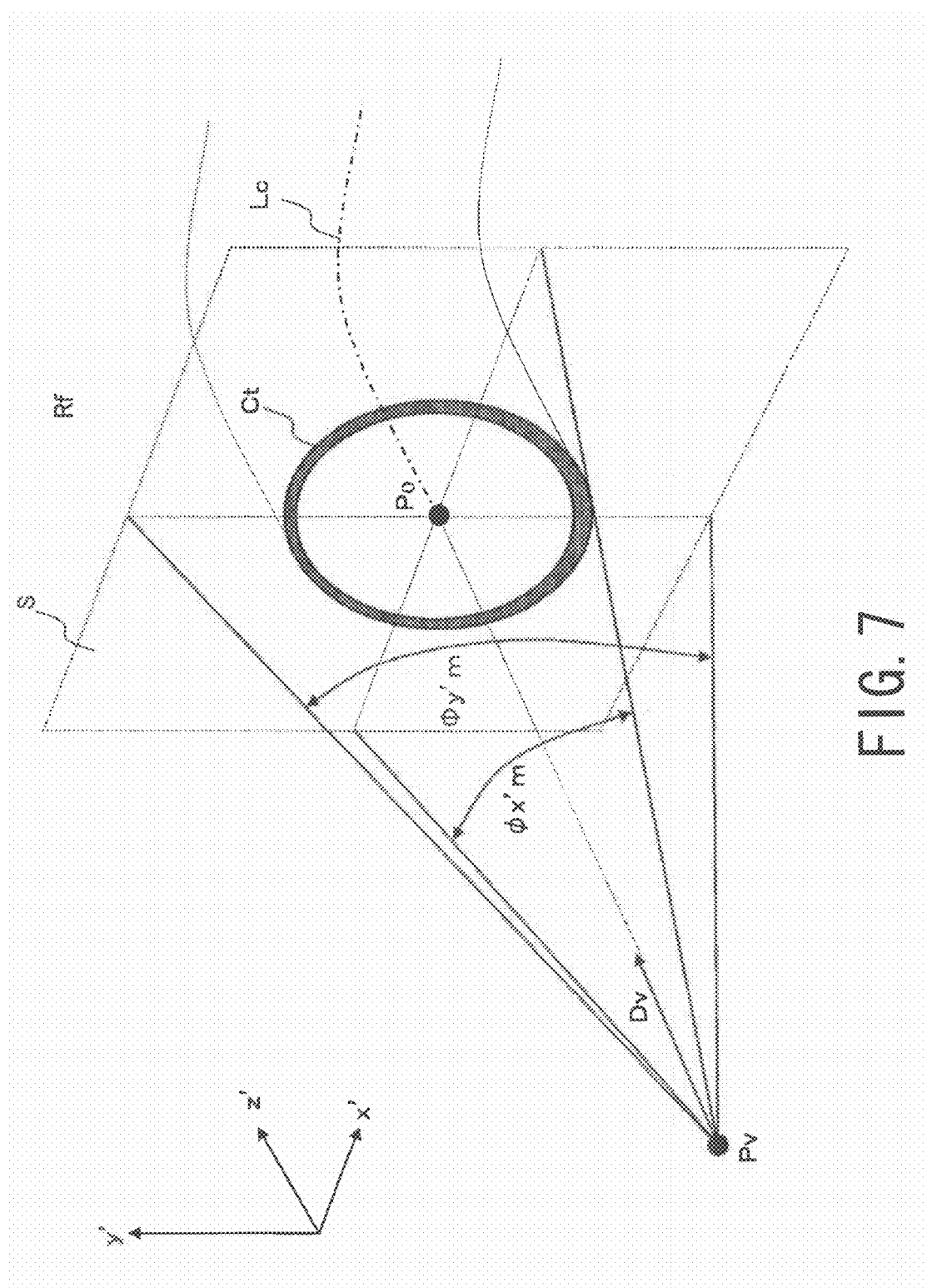
FIG. 7 is a diagram for illustrating a virtual endoscopic image data generation region set for the volume data according to the embodiment, FIGS. 8A and 8B include diagrams showing a cross section set for the volume data by a cross section setting unit according to the embodiment.

FIG. 7 shows an image-data generation region Rf for the virtual endoscopic image data. The image data generation region Rf is set for the volume data Vd. As described above, the viewpoint Pv and the view direction Dv are set on the tangent line of the center line Lc at the reference point Po on the reference plane S, and a field-of-view range $\phi x'm$ in an x' direction and a field-of-view range $\phi y'm$ in a y' direction are set with respect to the view direction Dv. The calculation circuit in the virtual endoscopic image data generating unit 11 extracts volume data in the image data generation region Rf within the field-of-view ranges $\phi x'm$ and $\phi y'm$ set in the volume data Vd, and performs rendering of the extracted volume data based on the viewpoint Pv and the view direction Dv to generate virtual endoscopic image data. In this example, the input unit 16 sets the field-of-view range $\phi x'm$ in the x' direction and the field-of-view $\phi y'm$ in the y' direction in such a manner that the image data generation region Rf includes the contour Ct of the lumen of the organ in the reference plane S.

In this case, if the distance between the viewpoint Pv and the reference point Po is sufficiently long, the generated virtual endoscopic image data is parallel projection data. On the other hand, if the distance is short, the generated virtual endoscopic image data is perspective projection data that provides perspective.

Figure 8A:
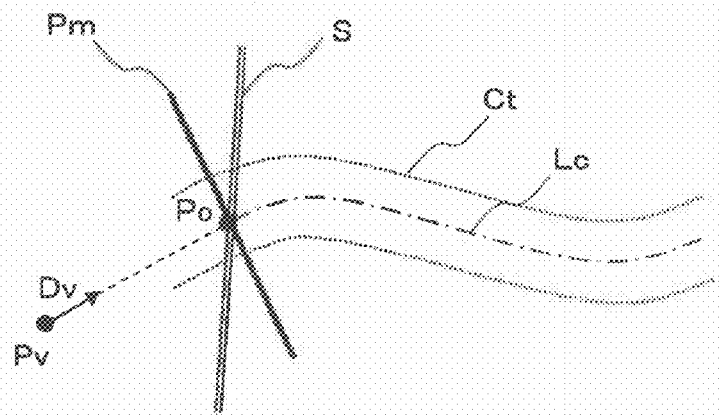
Figure 8B:
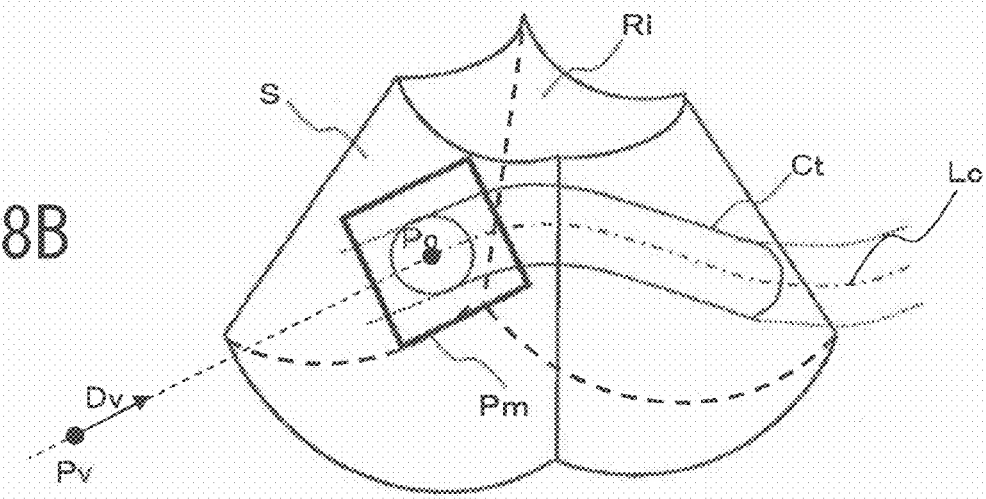

The cross section setting unit 12 shown in FIG. 1 reads the volume data from the volume data storage part 53 in the volume data generating unit 5 and sets, for the volume data, an axial cross section that includes the reference point, which is set at the intersection of the reference plane of the three-dimensional region of interest and the center line, and that is perpendicular to the center line (that is, perpendicular to the direction of the tangent line described above). FIGS. 8A and 8B show an axial cross section Pm set for the volume data. As described above, the cross section Pm set for the volume data includes the reference point Po set at the intersection of the center line Lc and the reference plane S of the three-dimensional region of interest Ri detected by the reference point detecting unit 9 and is perpendicular to the center line Lc. The axial cross section Pm set in this step and the reference plane S of the three-dimensional region of interest Ri do not always agree with each other, as can be seen from FIG. 8A.

Then, the cross-sectional image data generating unit 13 shown in FIG. 1 extracts voxels of the volume data included in the axial cross section Pm set by the cross section setting unit 12 or located in the vicinity of the axial cross section Pm, and performs data processing, such as filtering and interpolation, on the voxels to generate cross-sectional image data that represents an axial cross section of the lumen of the organ.

The three-dimensional image data generating unit 14 includes an opacity/color-tone setting part and a rendering part (both not shown). The opacity/color-tone setting part sets opacity and a color tone based on voxel values of the volume data read from the volume data storage part 53 in the volume data generating unit 5. The rendering part performs rendering of the volume data based on the opacity and the color tone set by the opacity/color-tone setting part to generate three-dimensional image data, such as volume rendering image data and surface rendering image data. The three-dimensional image data generating unit 14 further includes a data inversion part (not shown) in addition to the opacity/color-tone setting part and the rendering part (both not shown). The data inversion part inverts the voxel values of the volume data read from the volume data storage part 53 in the volume data generating unit 5. For example, if the voxel values range from 0 to 255, a voxel value of 0 is inverted to 255, a voxel value of 1 is inverted to 254, a voxel value of 2 is inverted to 253, a voxel value of 255 is inverted to 0, and so on. Based on the inverted voxel values, in the same way as described above, the opacity/color-tone setting part sets the opacity and the color tone, and the rendering part performs rendering, thereby producing the three-dimensional image data. The three-dimensional image data generated in this case is three-dimensional data on the lumen of the organ in which a lumen part is indicated by high brightness. The three-dimensional image data is generated by rendering of a three-dimensional image of the three-dimensional region of interest Ri including the lumen of the organ and a peripheral tissue surrounding the three-dimensional region of interest Ri and is generated independently of the virtual endoscopic image data and the cross-sectional image data described above.

The display unit 15 includes a display data producing part 151, a data conversion part 152, and a monitor 153. The display data producing part 151 generates first display data, which is intended to specify the reference plane, by superposing information on the three-dimensional region of interest set by the region-of-interest setting unit 8 on the three-dimensional image data generated by the three-dimensional image data generating unit 14. Furthermore, the display data producing part 151 generates second display data, which is intended for diagnosis of the object, by combining the virtual endoscopic image data generated by the virtual endoscopic image data generating unit 11 and the cross-sectional image data generated by the cross-sectional image data generating unit 13 and adding auxiliary information, such as object information, to the resulting image data. The data conversion part 152 performs conversion, such as display format conversion and D/A conversion, of the first display data and the second display data generated by the display data producing part 151, and the monitor 153 provides display of the resulting data.

Figure 9:
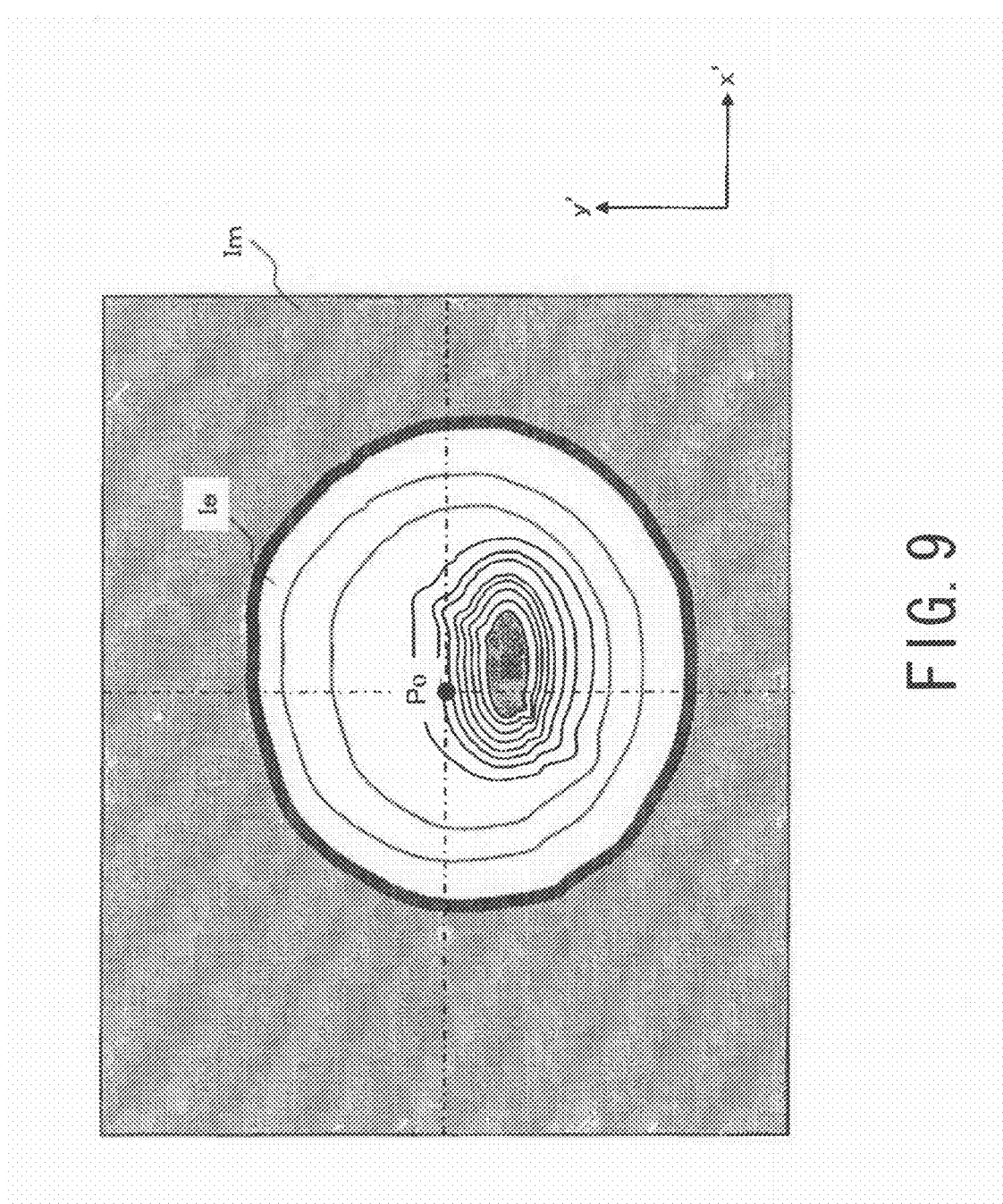
FIG. 9 is a diagram showing a specific example of second display data generated by a display unit according to the embodiment combining the virtual endoscopic image data and cross-sectional image data.

FIG. 9 shows a specific example of the second display data generated by the display data producing part 151. The second display data is generated by combining virtual endoscopic image data Ie and cross-sectional image data Im in such a manner that the reference point Po (that is, the view direction Dv) in the virtual endoscopic image data Ie and the reference point Po in the cross-sectional image data Im agree with each other and adding auxiliary information (not shown), such as object information and image data generation condition information, to a periphery of the combined data. That is, the second display data is generated by superposing the virtual endoscopic image data Ie representing an inner wall surface of the lumen of the organ acquired in the field-of-view range $\phi$x'm in the x' direction and the field-of-view range $\phi$y'm in the y' direction with respect to the viewpoint Pv and the view direction Dv on the cross-sectional image data Im representing an axial cross section of the lumen of the organ and a peripheral organ acquired in the axial cross section that includes the reference point Po and is perpendicular to the center line. In this case, the display data is generated so that the reference point Po is always displayed at a central part of the monitor 153 even if the ultrasonic probe 3 moves.

The input unit 16 shown in FIG. 1 includes a display panel and input devices including a keyboard, a track ball, a mouse, a select button and an input button arranged on an operation panel. The input unit 16 has a reference plane specifying function 161 that specifies the reference plane of the three-dimensional region of interest and an origin setting function 162 that sets an origin used for setting the center line in the lumen of the organ represented by the volume data. The display panel and the input devices are used to input object information, to set a volume data generation condition, a three-dimensional image data generation condition, a virtual endoscopic image data generation condition and a cross-sectional image data generation condition, to set the distance R between the reference point and the viewpoint, to set the field-of-view ranges $\phi$x'm and $\phi$y'm, and to input various command signals, for example.

The scan control unit 17 controls the delay times of the transmission delay circuit 212 in the transmission part 21 and the reception delay circuit 222 in the reception part 22 for performing successive transmission/reception of an ultrasonic wave to/from the three-dimensional region in the object. The system control unit 18 includes a CPU and a storage circuit (both not shown). The storage circuit stores the above-described various kinds of information input, set or specified via the input unit 16. Under the collective control of the CPU based on the above-described various kinds of information, the units of the ultrasonic image diagnosis system 100 generate and display the virtual endoscopic image data, the three-dimensional image data and the cross-sectional image data.

(Generation/Display Procedure for Virtual Endoscopic Image Data)

Next, a generation/display procedure for the virtual endoscopic image data according to this embodiment will be described with reference to the flowchart of FIG. 10.

Figure 10:
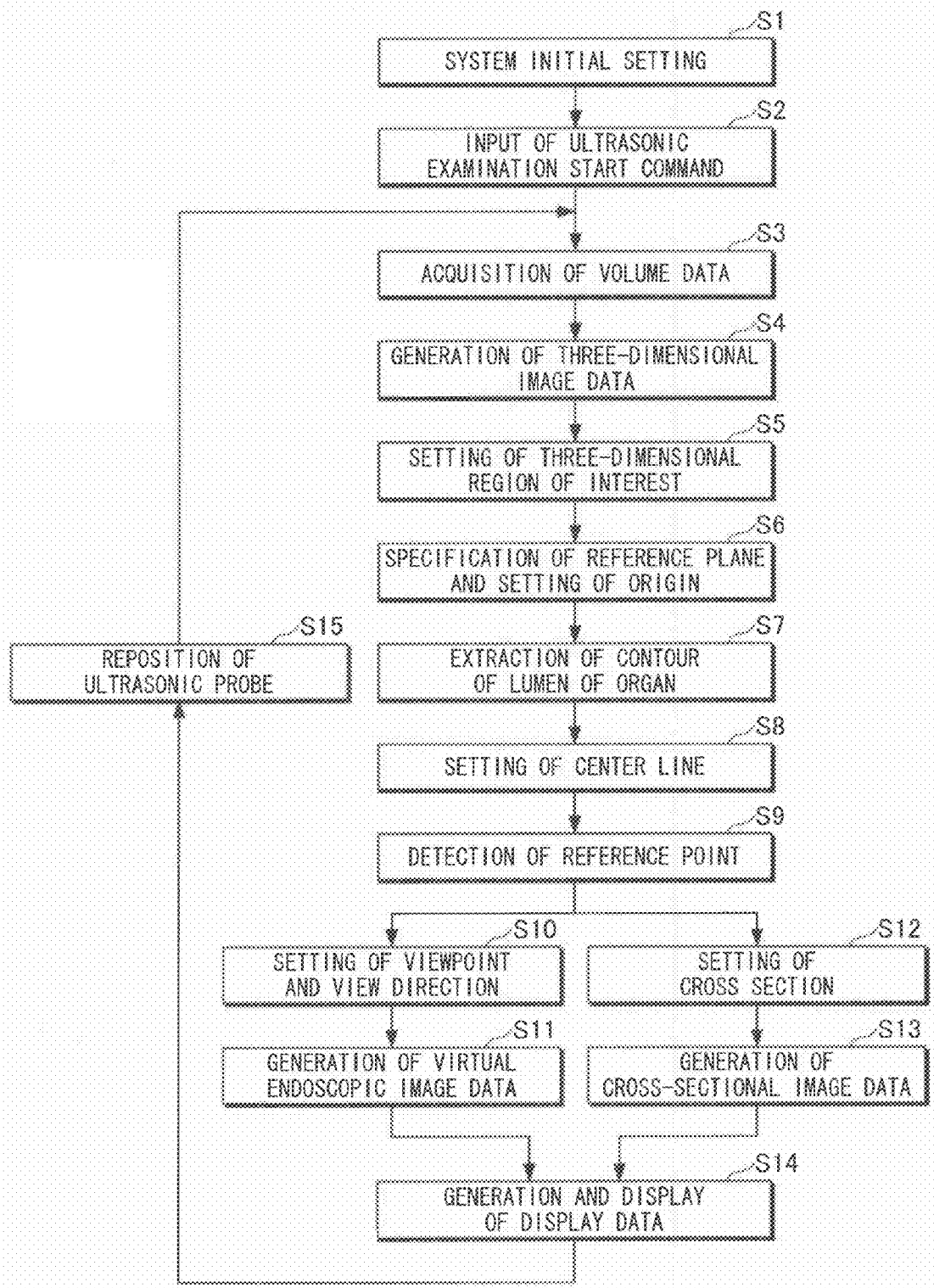
FIG. 10 is a flowchart showing a generation/display procedure for the virtual endoscopic image data according to the embodiment, FIGS. 11A and 11B include diagrams showing modifications of the viewpoint and the view direction set for the volume data by the viewpoint/view-direction setting unit according to the embodiment.

In advance of ultrasonic examination of the object, an operator of the ultrasonic diagnosis system 100 operates the input unit 16 to input the object information and set the volume data generation condition, the three-dimensional image data generation condition, the virtual endoscopic image data generation condition, the cross-sectional image data generation condition, the field-of-view ranges $\phi$x'm and $\phi$y'm, the distance R between the reference point and the viewpoint and the like, and places the ultrasonic probe 3 at a preferred position on a body surface of the object (step S1 in FIG. 10).

Upon completion of the initial setting described above, the operator operates the input unit 16 to input a start command to start ultrasonic examination (step S2 in FIG. 10). In response to supply of the command signal, the system control unit 18 starts acquisition of volume data on the diagnosis target part (lumen of the organ) of the object.

More specifically, the rate pulse generator 211 in the transmission part 21 shown in FIG. 2 performs frequency division of the reference signal supplied from the system control unit 18 to generate a rate pulse and supplies the rate pulse to the transmission delay circuit 212. The transmission delay circuit 212 provides the rate pulse with the focusing delay time required to focus the ultrasonic wave at a predetermined depth and the deflecting delay time required to transmit the ultrasonic wave in an initial transmission/reception direction (θx1, φy1), and supplies the resulting rate pulse to the Mt-channel drive circuit 231. Then, the drive circuit 213 generates a drive signal based on the rate pulse supplied from the transmission delay circuit 212, and supplies the drive signal to Mt transmission acoustic elements 31 in the ultrasonic probe 3 to make the elements emit a transmission ultrasonic wave into the object.

Part of the emitted transmission ultrasonic wave is reflected from an organ boundary or tissue at which the acoustic impedance varies, and the Mr receiving acoustic elements 31 in the ultrasonic probe 3 receive the reflected ultrasonic wave and convert the wave into Mr channels of electrical received signals. Then, the A/D converter 221 in the reception part 22 converts the received signals into digital signals, and the Mr-channel reception delay circuit 222 provides the digital signals with the converging delay time required to converge the reception ultrasonic waves from the predetermined depth and the deflecting delay time required to set an intense reception directivity to the reception ultrasonic wave from the transmission/reception direction (φx1, φy1). After that, the adder 223 performs phase-adjusting and summation of the resulting signals.

The phase-adjusted and summed received signal is supplied to the received signal processing unit 4, and the envelope detector 41 and the logarithmic converter 42 in the received signal processing unit 4 perform envelope detection and logarithmic conversion on the received signal to generate B-mode data as ultrasonic wave data. The ultrasound data storage part 51 in the volume data generating unit 5 stores the B-mode data along with the transmission/reception direction (φx1, φy1) as auxiliary information.

Upon completion of generation and storage of the ultrasonic wave data for the transmission/reception direction (θx1, φy1), the scan control unit 17 controls the delay times of the transmission delay circuit 212 in the transmission part 21 and the reception delay circuit 222 in the reception part 22 in response to the indication signal supplied from the system control unit 18, thereby successively updating the transmission/reception direction (θxp, θyq) (θxp=φx1+(p−1)Δθx (p=1 to P), φyq=θy1+(q−1)Δθy (q=1 to Q), except for the transmission/reception direction (θx1, θy1)) in increments of Δθx and Δθy, respectively, so that transmission and reception of the ultrasonic wave occur successively in those directions to achieve three-dimensional scan. The ultrasonic wave data storage part 51 also stores the ultrasonic data for these transmission/reception directions along with the transmission/reception directions as auxiliary information.

The interpolation processing part 52 in the volume data generating unit 5 reads a plurality of pieces of ultrasonic data from the ultrasonic data storage part 51, arranges the pieces of ultrasonic data in relation to the transmission/reception directions (θxp, θyq) (θxp=θx1+(p−1)Δθx (p=1 to P), θyq=θy1+ (q−1)Δθy (q=1 to Q)) to generate three-dimensional ultrasonic data, and interpolates between the pieces of ultrasonic data to generate volume data. The volume data storage part 53 stores the generated volume data (step S3 in FIG. 10).

Upon completion of acquisition of the volume data for the object, the three-dimensional image data generating unit 14 sets the opacity and the color tone based on the voxel values of the volume data read from the volume data storage part 53 in the volume data generating unit 5, and performs rendering of the volume data based on the opacity and the color tone, thereby producing three-dimensional image data (step S4 in FIG. 10).

The region-of-interest setting unit 8 receives the volume data generation condition supplied from the system control unit 18 via the input unit 16, and sets a three-dimensional region of interest having a region size [θxb, θyb] (see FIG. 5) corresponding to the region size for the volume data (step S5 in FIG. 10). Then, the display data producing part 151 in the display unit 15 generates first display data by superposing the information on the three-dimensional region of interest supplied from the region-of-interest setting unit 8 on the three-dimensional image data supplied from the three-dimensional image data generating unit 14, and displays the first display data on the monitor 153.

Upon observing the three-dimensional image data on which the three-dimensional region of interest information is superposed (that is, the first display data) on the display unit 15, the operator operates the input unit 16 to specify a reference plane of the three-dimensional region of interest with which the lumen of the organ on the three-dimensional image data intersects, and sets an origin used for setting of a center line in the lumen of the organ (step S6 in FIG. 10).

The contour extracting unit 6 extracts a contour of the lumen of the organ based on the spatial variation of the voxel values of the volume data read from the volume data storage part 53 in the volume data generating unit 5 (step S7 in FIG. 10), and the center line setting unit 7 receives the positional information on the origin set via the input unit 16 via the system control unit 18, and sets a center line of the lumen of the organ based on the search vector set in the lumen of the organ represented by the volume data with respect to the origin described above (step S8 in FIG. 10).

Then, the reference point detecting unit 9 detects a reference point at which the reference plane of the three-dimensional region of interest specified via the input unit 16 and the center line of the lumen of the organ set by the center line setting unit 7 intersect with each other (step S9 in FIG. 10), and the viewpoint/view-direction setting unit 10 sets a viewpoint and a view direction required to generate virtual endoscopic image data based on the reference point on the reference plane detected by the reference point detecting unit 9 and the tangential direction of the center line at the reference point (step S10 in FIG. 10).

Then, the virtual endoscopic image data generating unit 11 reads the volume data on the object stored in the volume data storage part 53 in the volume data generating unit 5 and the calculation program stored in the storage circuit therein, and generates virtual endoscopic image data by performing rendering of the volume data based on the information on the three-dimensional region of interest supplied from the region-of-interest setting unit 8 and the information on the viewpoint and the view direction supplied from the viewpoint/view-direction setting unit 10 (step S11 in FIG. 10).

On the other hand, upon detection of the reference point at which the reference plane of the three-dimensional region of interest and the center line intersect with each other in step S9 as described above, the cross section setting unit 12 reads the volume data from the volume data storage part 53 in the volume data generating unit 5 and sets, for the volume data, an axial cross section that includes the reference point and is perpendicular to the center line (step S12 in FIG. 10). Then, the cross-sectional image data generating unit 13 extracts voxels of the volume data included in the axial cross section set by the cross section setting unit 12 or located in the vicinity of the axial cross section, and performs data processing, such, as filtering and interpolation, on the voxels to generate cross-sectional image data that represents an axial cross section of the lumen of the organ (step S13 in FIG. 10).

Then, the display data producing part 151 in the display unit 15 combines the virtual endoscopic image data generated by the virtual endoscopic image data generating unit 11 and the cross-sectional image data generated by the cross-sectional image data generating unit 13, and generates second display data by adding auxiliary information, such as the object information, to the resulting data. A predetermined conversion is performed on the second display data, and the resulting data is displayed on the monitor 153 (step S14 in FIG. 10).

After completion of generation and display of the virtual endoscopic image data or the like based on the volume data acquired with the ultrasonic probe 3 placed at the initial position according to the procedure described above, the position of the ultrasonic probe 3 is changed along the body surface of the object (step S15 in FIG. 10), and the steps S3 to S14 (excluding the step S6) are repeated each time the ultrasonic probe 3 is repositioned. As the ultrasonic probe 3 moves, the virtual endoscopic image data is updated so as to be viewed in the desired direction, that is, in the tangential direction of the center line of the lumen of the organ, and thus can be observed in real time.

According to the embodiment of the present invention described above, when the virtual endoscopic image data is generated based on the volume data acquired from the object, the viewpoint and the view direction are automatically set based on the intersection of the reference plane of the three-dimensional region of interest and the center line of the lumen of the organ represented by the volume data, which is updated while the ultrasonic probe moves. As a result, despite the movement of the ultrasonic probe, the virtual endoscopic image data can be always observed from a preferred direction in real time. Thus, the precision and efficiency of the diagnosis are substantially improved.

In addition, even if the viewpoint is set outside the three-dimensional region of interest, since the cross-sectional image data on the axial cross section and the virtual endoscopic image data can be displayed in combination, information on a periphery of the lumen of the organ can be grasped at the same time, so that the diagnosis precision is further improved. For example, in diagnosis of a tumor in a lumen of the organ, not only the tumor inside the lumen of the organ can be observed from the virtual endoscopic image data, but also tumor infiltration at an outer periphery of the lumen of the organ can be observed from the cross-sectional image data. Thus, the diagnosis precision is improved.

Further, the second display data is generated so as to ensure that the reference point and the view direction are always located at a predetermined position (a central part, for example) on the monitor. Therefore, even if the ultrasonic prove moves, the virtual endoscopic image data from the view direction can be steadily observed without a significant influence of the movement of the ultrasonic probe. As a result, the operator can perform ultrasonic examination with a reduced burden.

Figure 11A:
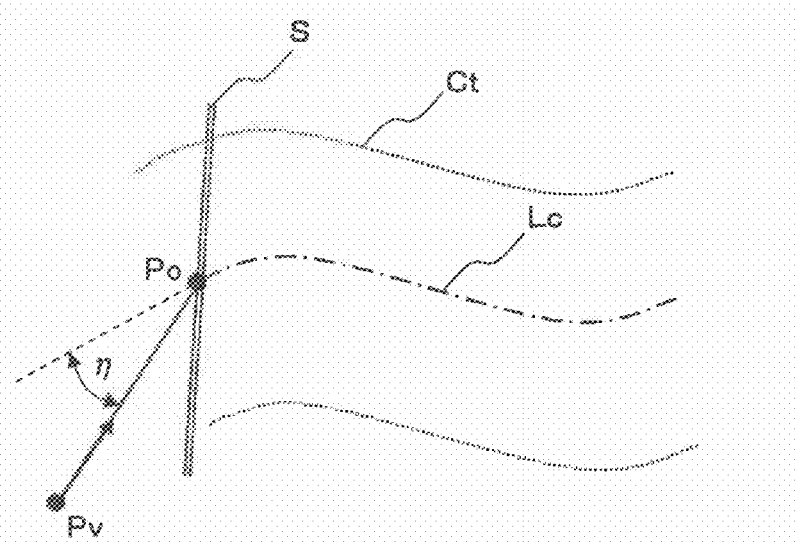
Figure 11B:
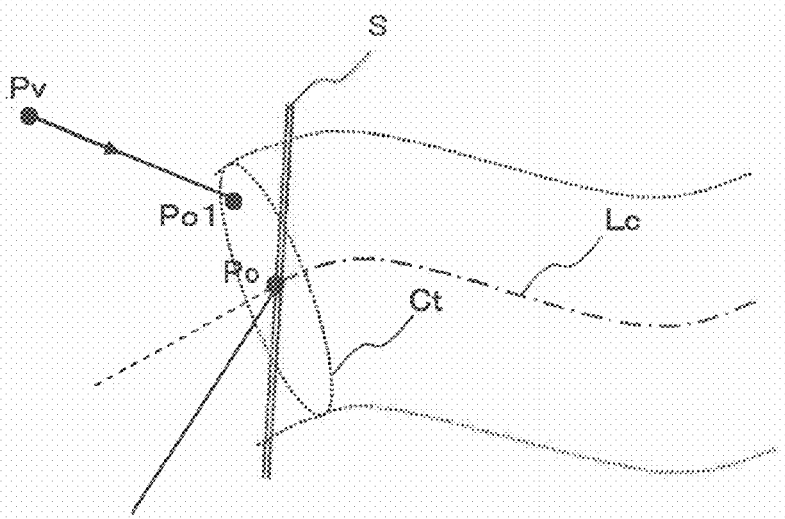

Although an embodiment of the present invention has been described above, the present invention is not limited to the embodiment, and various modifications can be made. In the embodiment described above, the tangential direction of the center line set by the center line setting unit 7 at the reference point is detected, and the view point for the virtual endoscopic image data is set at a position at a predetermined distance from the reference point in the tangential direction. However, for example, as shown in FIG. 11A, the viewpoint Pv may be set at a position at a predetermined distance from the reference point in a direction at a predetermined angle η with respect to the tangential direction. Alternatively, as shown in FIG. 11B, a second reference point Po1 may be set inside the lumen of the organ contour Ct defined by a closed loop on the cross section set to include the reference point Po, and the viewpoint Pv may be set at an arbitrary distance in an arbitrary direction with respect to the second reference point Po1. The second reference point Po1 may not be always located on the cross section but may be set at an arbitrary distance in an arbitrary direction with respect to the reference point Po.

In the embodiment described above, the viewpoint Pv is set outside the three-dimensional region of interest Ri. However, the viewpoint Pv may be set on the reference plane S of the three-dimensional region of interest Ri (that is, the viewpoint Pv may agree with the reference point Po) or even inside the three-dimensional region of interest Ri. In particular, in the case where the viewpoint Pv is set inside the three-dimensional region of interest Ri, the viewpoint Pv is set at a position inward from the reference point Po by a predetermined distance along the center line Lc, and the view direction Dv is preferably set to be the tangential direction of the center line Lc at the view point Pv. However, the present invention is not limited to this implementation. Note that in this case, generation of the cross-sectional image data is not necessarily essential.

In the embodiment described above, the three-dimensional region of interest is automatically set based on the volume data generation condition. However, the three-dimensional region of interest may be arbitrarily set by the operator using the input device of the input unit 16 while observing the three-dimensional image data displayed on the display unit 15. In addition, although the three-dimensional region of interest has been described as being set inside the volume data, the three-dimensional region of interest may have substantially the same size as the volume data.

Furthermore, the reference plane S may be set inside the three-dimensional region of interest Ri, rather than set on the particular side face of the three-dimensional region of interest Ri. For example, the reference plane S may be a scanning plane on which two-dimensional scan is to be performed when the ultrasonic probe for 3D scan is used in a 2D scan mode. In this case, even when the ultrasonic probe is moving, the reference plane S agrees with the two-dimensional cross section with which the operator is familiar, so that the operator can easily intuitively grasp the position of the viewpoint and the view direction.

Although the reference plane of the three-dimensional region of interest has been described as being set by the operator while observing the three-dimensional image data on which the information on the three-dimensional region of interest is superposed, the reference plane may be set in advance of ultrasonic examination as one of volume data generation conditions.

Figure 12:
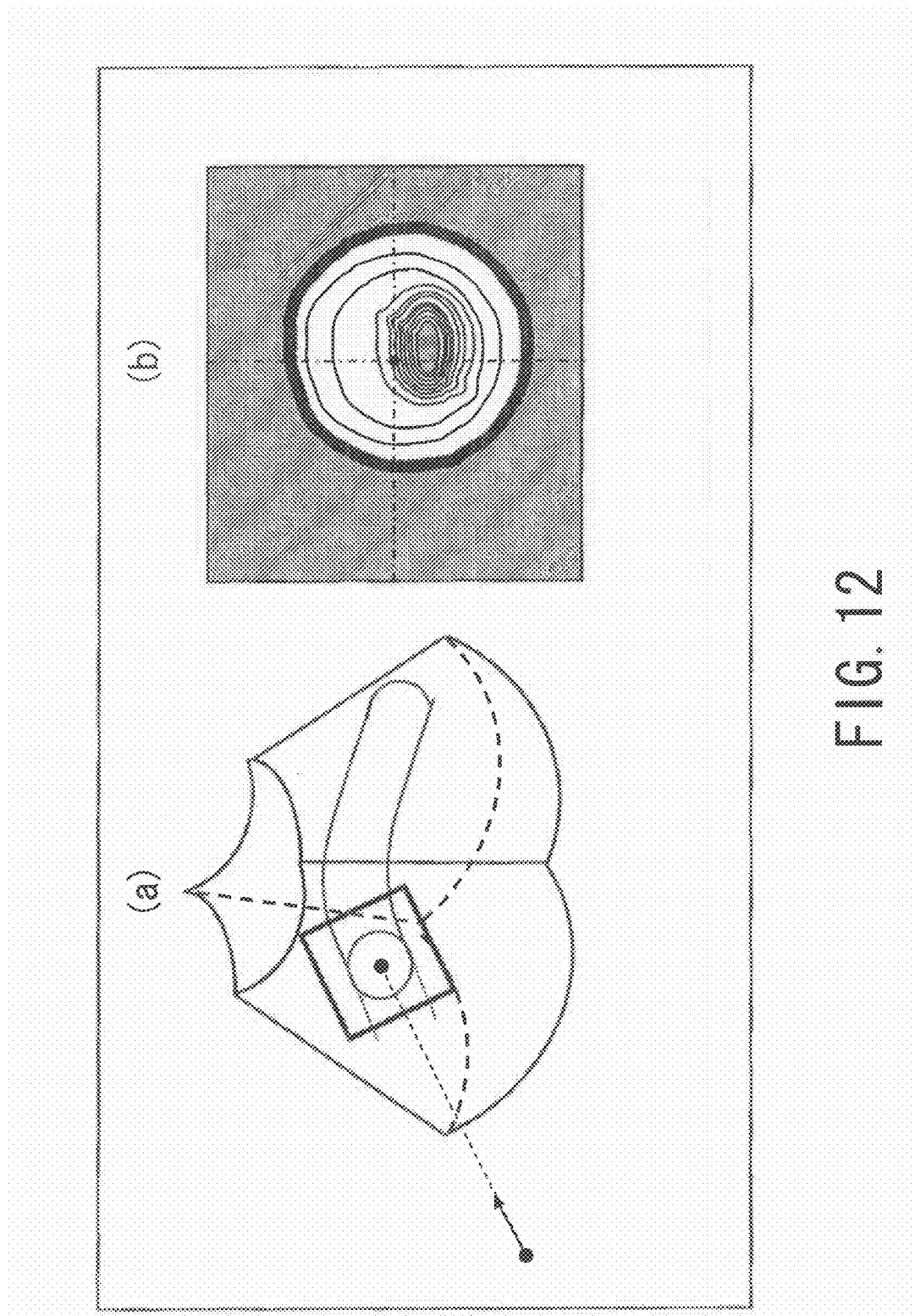
FIG. 12 is a diagram showing a modification of the second display data generated by the display unit according to the embodiment.

In the example described above, the second display data is generated by combining the virtual endoscopic image data and the cross-sectional image data when the viewpoint is set outside the three-dimensional region of interest. However, even when the viewpoint is set outside the three-dimensional region of interest, the second display data may not include the cross-sectional image data as when the viewpoint is set inside the three-dimensional region of interest. Furthermore, in the example described above, the second display data is the virtual endoscopic image data or a combination of the virtual endoscopic image data and the cross-sectional image data. However, the second display data may further include the three-dimensional image data as shown in FIG. 12. In this case, the three-dimensional image data ((a) in FIG. 12) and the virtual endoscopic image data or the virtual endoscopic image data with the cross-sectional image data superposed thereon ((b) in FIG. 12) are displayed simultaneously, for example, side by side, on the monitor 153 of the display unit 15.

In the embodiment described above, the volume data is generated based on three-dimensional B-mode data acquired with a two-dimensional array ultrasonic probe having a two-dimensional array of oscillating elements, and the virtual endoscopic image data and the cross-sectional image data are generated based on the volume data. However, the present invention is not limited to this implementation. For example, the image data may be generated based on volume data acquired by mechanically moving an ultrasonic probe having a one-dimensional array of oscillating elements. Alternatively, volume data based on ultrasonic data other than the B-mode data, such as color Doppler data, may be used.

While certain embodiments have been described, these embodiments have been presented by way of example only, and are not intended to limit the scope of the invention. Indeed, the novel apparatuses and units described herein may be embodied in a variety of other forms; furthermore, various omissions, substitutions and changes in the form of the apparatuses and units described herein may be made without departing from the spirit of the invention. The accompanying claims and their equivalents are intended to cover such forms or modifications as would fall within the scope and spirit of the invention.

What is claimed is:

1. An ultrasonic diagnosis system that generates virtual endoscopic image data of a lumen of an organ of an object based on volume data acquired by three-dimensional scanning using an ultrasonic probe, comprising:
   a region-of-interest setting unit that sets a three-dimensional region of interest for the volume data, the volume data being updated while the ultrasonic probe moves, and the three-dimensional region of interest being moved together with movement of the ultrasonic probe and being automatically set on the basis of an x-directional range and a y-directional range of the volume data;
   a center line setting unit that sets a center line of the lumen of the organ in the volume data based on the acquired volume data;
   a reference point detecting unit that detects a reference point at which a reference plane of the moved three-dimensional region of interest and the center line intersect with each other;
   a view setting unit that sets a viewpoint and a view direction based on the reference point;
   a virtual endoscopic image data generating unit that processes the volume data based on the viewpoint and the view direction to generate the virtual endoscopic image data; and
   a display unit that displays the generated virtual endoscopic image data.

2. The ultrasonic diagnosis system according to claim 1, wherein the three-dimensional scanning for acquiring the volume data is performed by continuously scanning a three-dimensional space in real time.

3. The ultrasonic diagnosis system according to claim 1, wherein the volume data is acquired by performing the three-dimensional scan while moving an ultrasonic probe with respect to the object.

4. The ultrasonic diagnosis system according to claim 1, further comprising:
   a reference plane specifying unit that specifies the reference plane of the three-dimensional region of interest, wherein the reference plane specifying unit specifies a side face of the three-dimensional region of interest that intersects with the lumen of the organ represented by the volume data as the reference plane.

5. The ultrasonic diagnosis system according to claim 1, further comprising:
   a reference plane specifying unit that specifies the reference plane of the three-dimensional region of interest, wherein the reference plane specifying unit specifies a scanning plane as the reference plane, the scanning plane being a plane on which two-dimensional scan is to be performed when the ultrasonic probe for the three-dimensional scan is used in a two-dimensional scan mode.

6. The ultrasonic diagnosis system according to claim 1, further comprising:
   a contour extracting unit that extracts a contour of the lumen of the organ based on a voxel value of the volume data,
   wherein the center line setting unit sets the center line of the lumen of the organ based on information on the contour extracted by the contour extracting unit.

7. The ultrasonic diagnosis system according to claim 1, wherein the view setting unit sets the viewpoint and the view direction based on the reference point detected by the reference point detecting unit and a tangential direction of the center line at the reference point.

8. The ultrasonic diagnosis system according to claim 7, wherein the view setting unit sets the viewpoint at a position away from the reference point at a predetermined distance in the tangential direction or a direction at a predetermined angle with respect to the tangential direction, and sets the view direction in a direction from the viewpoint to the reference point.

9. The ultrasonic diagnosis system according to claim 7, wherein the view setting unit sets the viewpoint at the reference point and sets the view direction to be the tangential direction of the center line at the reference point or a direction at a predetermined angle with respect to the tangential direction.

10. The ultrasonic diagnosis system according to claim 1, further comprising:
    a cross section setting unit that sets an axial cross section that includes the reference point and is perpendicular to the center line for the volume data; and
    a cross-sectional image data generating unit that extracts a voxel of the volume data in the axial cross section to generate cross-sectional image data,
    wherein the display unit displays a combination of the cross-sectional image data and the virtual endoscopic image data.

11. The ultrasonic diagnosis system according to claim 1, further comprising:
    a three-dimensional image data generating unit that generates three-dimensional image data by rendering of the volume data,
    wherein the display unit displays the virtual endoscopic image data and the three-dimensional image data simultaneously.

12. The ultrasonic diagnosis system according to claim 10, further comprising:
    a three-dimensional image data generating unit that generates three-dimensional image data by rendering of the volume data, wherein the display unit displays the virtual endoscopic image data on which the cross-sectional image data is superposed and the three-dimensional image data simultaneously.

13. The ultrasonic diagnosis system according to claim 1, wherein the display unit has a monitor that displays the virtual endoscopic image data, and the virtual endoscopic image data is displayed with the reference point in the virtual endoscopic image data being always located at a predetermined position on the monitor.

14. The ultrasonic diagnosis system according to claim 1, wherein the virtual endoscopic image data generating unit generates the virtual endoscopic image data by performing rendering of the volume data based on the viewpoint and the view direction.

15. A non-transitory computer-readable medium storing an image data display control program that is executed by a processor, the processor being included in an ultrasonic diagnosis system that generates virtual endoscopic image data on a lumen of an organ of an object based on volume data acquired by three-dimensional scanning using an ultrasonic probe, comprising:
   setting a three-dimensional region of interest for the volume data which is, the volume data being updated while the ultrasonic probe moves, and the three-dimensional region of interest being moved together with movement of the ultrasonic probe and being automatically set on the basis of an x-directional range and a y-directional range of the volume data;
   setting a center line of the lumen of the organ represented by the volume data based on the volume data;
   detecting a reference point at which a reference plane of the moved three-dimensional region of interest and the center line intersect with each other;
   setting a viewpoint and a view direction based on the reference point;
   processing the volume data based on the viewpoint and the view direction to generate the virtual endoscopic image data; and
   displaying the generated virtual endoscopic image data.

16. An ultrasonic diagnosis system that generates virtual endoscopic image data of a lumen of an organ of an object based on volume data acquired by three-dimensional scanning using an ultrasonic probe, the volume data being updated while the ultrasonic probe moves, the system comprising:
   a center line setting unit that sets a center line of the lumen of the organ in the volume data based on the acquired volume data;
   a reference point detecting unit that detects a reference point at which a reference plane and the center line intersect with each other, the reference plane being moved together with movement of the ultrasonic probe and being set in the volume data as a scanning plane on which two-dimensional scan is to be performed when the ultrasonic probe is used in a two-dimensional scanning mode;
   a view setting unit that sets a viewpoint and a view direction based on the reference point;
   a virtual endoscopic image data generating unit that processes the volume data based on the viewpoint and the view direction to generate the virtual endoscopic image data; and
   a display unit that displays the generated virtual endoscopic image data.

* * * * *